(12) United States Patent
Maskin

(10) Patent No.: US 10,603,210 B1
(45) Date of Patent: Mar. 31, 2020

(54) MEIBOMIAN GLAND PROBING WITH BLOOD PRODUCT INJECTION

(71) Applicant: MGD Innovations, LLC, Tampa, FL (US)

(72) Inventor: Steven L. Maskin, Tampa, FL (US)

(73) Assignee: MGD INNOVATIONS, LLC, Tampa, FL (US)

( * ) Notice: Subject to any disclaimer, the term of this patent is extended or adjusted under 35 U.S.C. 154(b) by 99 days.

(21) Appl. No.: 15/887,406

(22) Filed: Feb. 2, 2018

Related U.S. Application Data

(60) Provisional application No. 62/453,804, filed on Feb. 2, 2017.

(51) Int. Cl.
| | | |
|---|---|---|
| *A61F 9/007* | (2006.01) | |
| *A61F 9/00* | (2006.01) | |
| *A61M 31/00* | (2006.01) | |
| *A61K 9/00* | (2006.01) | |
| *A61M 25/00* | (2006.01) | |

(52) U.S. Cl.
CPC ........ *A61F 9/00736* (2013.01); *A61F 9/0008* (2013.01); *A61M 31/00* (2013.01); *A61K 9/0048* (2013.01); *A61M 25/007* (2013.01); *A61M 2202/0413* (2013.01); *A61M 2202/0415* (2013.01); *A61M 2202/0423* (2013.01); *A61M 2202/0427* (2013.01); *A61M 2202/0462* (2013.01); *A61M 2210/0612* (2013.01)

(58) Field of Classification Search
CPC ................ A61M 31/00; A61M 31/002; A61M 2202/0021; A61M 2202/0413; A61M 2202/0415; A61M 2202/0423; A61M 2202/0427; A61M 2202/0462; A61M 2210/0612; A61M 25/007; A61F 9/0008; A61F 9/0017; A61F 9/0026; A61F 9/00736; A61F 9/00772; A61K 9/0048
See application file for complete search history.

(56) References Cited

U.S. PATENT DOCUMENTS

| | | |
|---|---|---|
| 3,834,391 A | 9/1974 | Block |
| 4,211,767 A | 7/1980 | Klein |
| 4,583,539 A | 4/1986 | Karlin et al. |
| 4,915,684 A | 4/1990 | MacKeen et al. |

(Continued)

FOREIGN PATENT DOCUMENTS

| | | |
|---|---|---|
| JP | 11-221247 | 8/1999 |
| WO | 9404155 | 3/1994 |
| WO | 2008076544 | 6/2008 |

OTHER PUBLICATIONS

Sharma et al, Fingerprick Autologous Blood (FAB) in Mebomian Gland Dysfunction (MGD), Oct. 24, 2016, ClinicalTrials.gov (Year: 2016).*

(Continued)

*Primary Examiner* — Shefali D Patel
(74) *Attorney, Agent, or Firm* — Allen Dyer Doppelt & Gilchrist, PA

(57) ABSTRACT

A method of improving meibomian gland function in a patient includes inserting a cannula into an interior of a meibomian gland of the patient through an orifice thereinto, the cannula including at least one opening in communication with the interior of the meibomian gland, and injecting a blood product into the interior of the meibomian gland through the inserted cannula via the at least one opening.

12 Claims, 1 Drawing Sheet

(56) References Cited

U.S. PATENT DOCUMENTS

| | | | |
|---|---|---|---|
| 5,283,063 A | 2/1994 | Freeman | |
| 6,235,016 B1 | 5/2001 | Stewart | |
| 6,344,047 B1 | 2/2002 | Price et al. | |
| 6,428,502 B1 | 8/2002 | Lang | |
| 6,936,053 B1 | 8/2005 | Weiss | |
| 7,211,070 B2 | 5/2007 | Soroudi | |
| 7,335,367 B2* | 2/2008 | Borodic | A61K 38/4893 424/184.1 |
| 7,678,065 B2 | 3/2010 | Haffner et al. | |
| 2002/0116750 A1 | 8/2002 | Korb | |
| 2003/0072711 A1 | 4/2003 | Korb | |
| 2003/0211043 A1 | 11/2003 | Korb | |
| 2004/0237969 A1 | 12/2004 | Fuller | |
| 2006/0058743 A1 | 3/2006 | Putz | |
| 2006/0153885 A1 | 7/2006 | Korb et al. | |
| 2006/0270621 A1 | 11/2006 | Christiano | |
| 2007/0016254 A1 | 1/2007 | Grenon et al. | |
| 2007/0016255 A1 | 1/2007 | Korb et al. | |
| 2007/0016256 A1 | 1/2007 | Korb et al. | |
| 2007/0027431 A1 | 2/2007 | Korb et al. | |
| 2007/0036726 A1 | 2/2007 | Korb et al. | |
| 2007/0260201 A1 | 11/2007 | Prausnitz et al. | |
| 2008/0081999 A1 | 4/2008 | Gravely et al. | |
| 2010/0100029 A1* | 4/2010 | Maskin | A61B 17/22 604/20 |
| 2010/0292630 A1 | 11/2010 | Maskin | |
| 2018/0098937 A1* | 4/2018 | Horn | A61K 9/0048 |

OTHER PUBLICATIONS

Geerling et al, Autologous serum eye drops for ocular surface disorders, Jun. 11, 2004, Br J Ophthalmol (Year: 2004).*

Tunay et al, Successful treatment of ligneous conjunctivitis with topical fresh frozen plasma in an infant, Sep./Oct. 2015, Arquivos Brasileiros de Oftalmologia (Year: 2015).*

Cowper, H.W.; Meibomian Seborrhea; American Journal of Opthalmology, vol. 5, Issue 1, Jan. 1922, pp. 25-30; Buffalo, N.Y.

Reinstein, et al.; Successful Treatment of Distichiasis in a Cat Using Transconjunctival Electrocautery; Veterinary Ophthalmology (2011) 14 Supplement 1, pp. 130-134; Philadelphia, PA.

Gelatt, Kirk N.; Diseases and Surgery of the Canine Eyelid; Veterinary Ophthalmology, 4th edition, vol. 2, Blackwell Publishing (2007), pp. 563-617; University of Florida, Gainesville, FL.

* cited by examiner

MEIBOMIAN GLAND PROBING WITH BLOOD PRODUCT INJECTION

CROSS-REFERENCE TO RELATED APPLICATION

This application claims the benefit of U.S. Provisional Patent Application Ser. No. 62/453,804, filed on Feb. 2, 2017, the contents of which are herein incorporated by reference in their entirety.

FIELD OF THE INVENTION

The present invention relates to the treatment of meibomian gland dysfunction and related ocular conditions, and more particularly, to treatment involving meibomian gland probing.

BACKGROUND OF THE INVENTION

Obstructive Meibomian gland dysfunction (o-MGD) is considered the most frequent cause of evaporative dry eye in the world. O-MGD is associated with aging and contact lens use, but is also associated with many causes of chronic ocular surface inflammation, including allergy and anterior blepharitis. Untreated, o-MGD will lead to atrophy of MGs characterized by infrared (IR) meibography changes, such as segments of discontinuous gland tissue, shortening of glands, and whole or partial gland dropout, leaving fading and poorly defined glands with an ultimate loss of all gland tissue. Symptoms develop from obstruction, causing elevated intraductal pressure, leading to lid tenderness and inflammation with subsequent lipid tear deficiency and dry eye. Treatment has classically focused on an anti-inflammatory approach using antibiotics and steroid along with lid hygiene using heat and lid margin cleansing with optional pressure to the lid to express glands and minimize lid margin inflammation and orifice obstruction. Eye drops are frequently employed in connection with treatments, including, in some cases, eye drops containing autologous serum (AS).

Recently, new approaches to try and reverse glandular obstruction have included thermal pulsation (as practiced under the third-party trademark Lipiflow) and Meibomian Gland Probing (MGP). Lipiflow-style thermal pulsation uses predetermined levels of external heat and pressure to try and force meibum through a duct and orifice obstructed by thickened meibum and intraluminal keratinized debris. In contrast, meibomian gland probing inserts sterile stainless steel wire probes through the natural gland orifice to physically and directly unblock the orifice and ductal obstruction from thickened meibum and other non-fibrotic sources of obstruction. Importantly, MGP also relieves fixed obstructions, such as multifocal periductal fibroses, which are thought to occur along the length of the gland.

Meibomian gland probing is generally described by the present inventor in U.S. patent application Ser. No. 12/305,094, filed on Oct. 18, 2010, the contents of which are herein incorporated by reference in their entirety. The use of MGP allows equilibration of intraductal pressures on both sides of the obstruction with immediate and dramatic relief of lid tenderness and release of sequestered meibum with improved tear break-up time (TBUT). MGP has also been shown to restore meibum secreting gland functionality, significantly increasing the numbers of expressible glands per lid and improve quality and quantity of meibum lipid.

The goal of treating o-MGD should not be limited to symptom relief and stabilizing age or disease associated gland atrophy, but rather to grow Meibomian glands (MGs) and restore a full, functional, healthy, and resilient MG lid population. Consequently, while existing therapies have shown a great deal of promise, further improvements are possible.

SUMMARY OF THE INVENTION

In view of the foregoing, it is an object of the present invention to enhance the efficacy of meibomian gland probing (MGP) for certain patients with the injection of a blood product via the gland orifice. According to an aspect of the present invention, the blood product includes autologous serum (AS).

These and other objects, aspects and advantages of the present invention will be appreciated in view of the drawings and following detailed description of preferred embodiments.

DETAILED DESCRIPTION OF PREFERRED EMBODIMENTS

Figure 1:
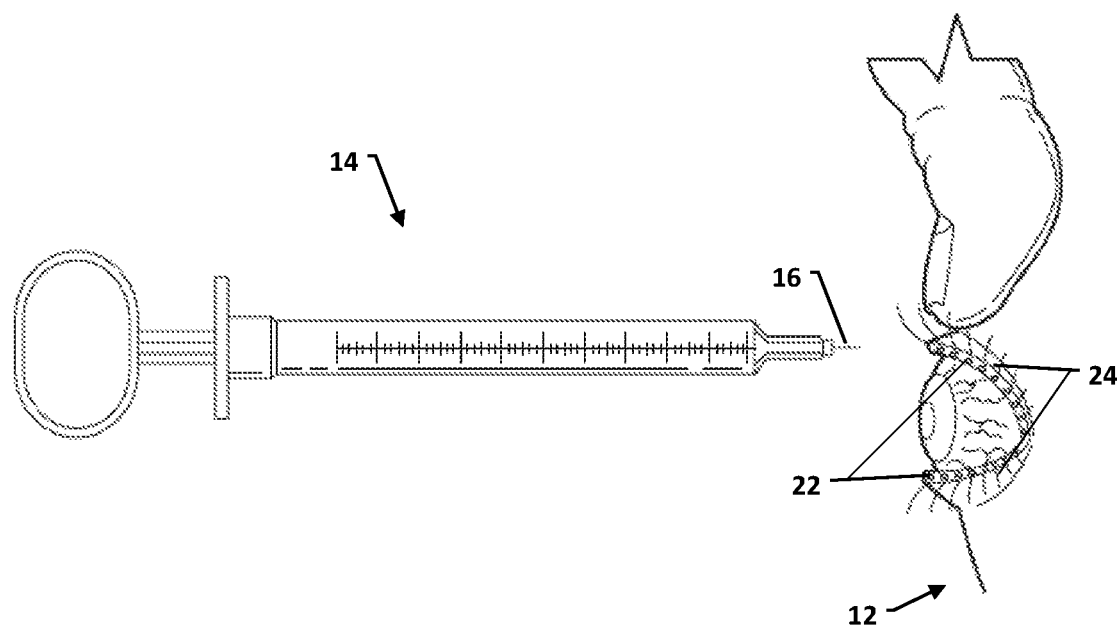
FIG. 1 is a side view of an eye and surrounding area of a patient prior to injection of blood products into one or more meibomian glands thereof.
Figure 2:
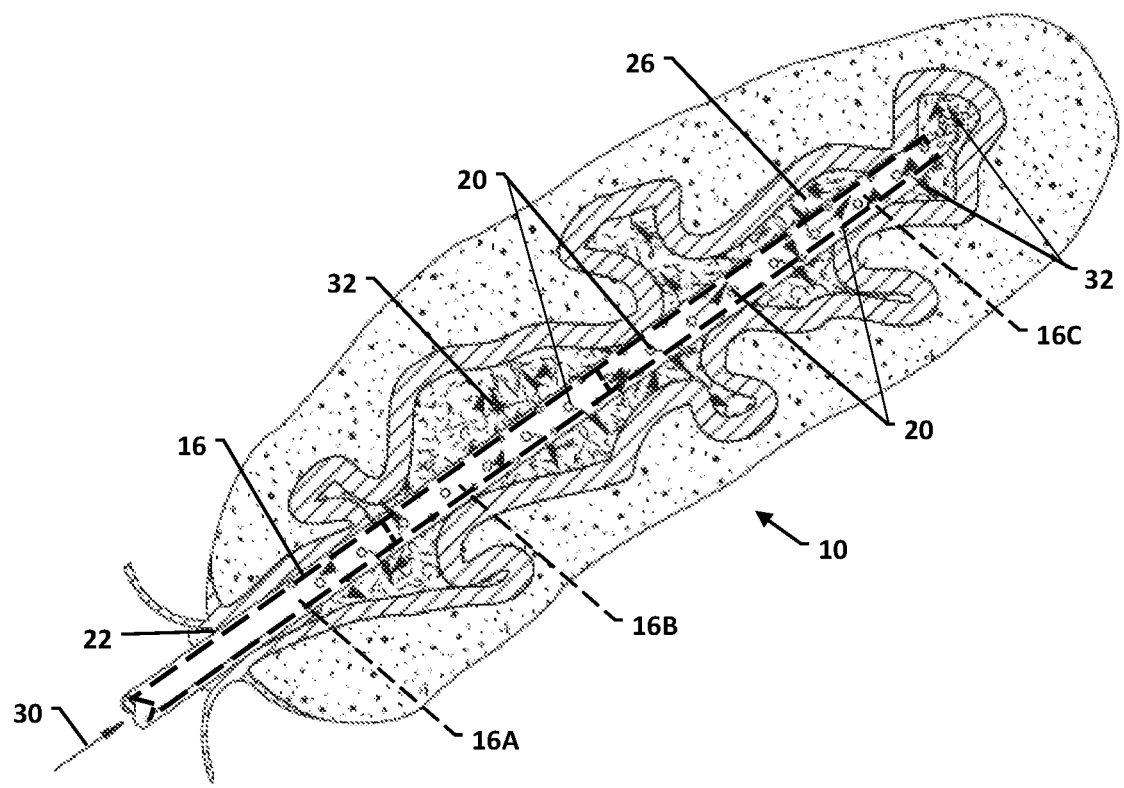
FIG. 2 is a sectional view of one of the meibomian glands of FIG. 1 receiving an injection of blood products via a probe inserted through the orifice thereof, according to an embodiment of the present invention.

According to a preferred embodiment of the present invention, referring to FIGS. 1 and 2, meibomian gland 10 function is improved in a patient 12 via injection of one or more blood products, either alone or in combination with other substances. A probe 14 includes a cannula 16 having one of more openings 20 is inserted into one of the meibomian glands 10 through its orifice 22 located in an eyelid 24 of the patient 12.

With the cannula 16 at least partially inserted, the openings 20 communicate with an interior 26 of the meibomian gland. The blood product is introduced into the cannula 16 as indicated by the arrow 30 and injected into the interior 26 of the meibomian gland 10 through the one or more openings 20 as indicated by the arrows 32. One or more preliminary probing steps can be performed before insertion of the cannula, typically with smaller probes. The process is repeated as necessary with the other meibomian glands. Multiple treatments of the same glands can also be performed over time.

In one working example, treatment beings with the application of one drop of topical 0.5% tetracaine hydrochloride on the inferior fornix followed by placing a bandage contact lens over the eye. Topical anesthetic ointment consisting of 8% lidocaine with 25% jojoba in a petrolatum ointment base, is applied to the inferior lid margin. The eye is closed for 15 minutes. One additional drop of topical tetracaine is then placed in the eye. The patient is then positioned at the slit lamp. The meibomian gland orifices are then visualized and examined.

A 1-mm long stainless steel sterile probe 16A is then inserted into each orifice, perpendicular to the lid margin using a dart throwing motion to find the angle of entry. Frequent "pops and gritty sounds" are heard by patient and physician as the periductal fibroses are released and the resistance gives way, allowing the probe to then freely pass to and fro within the duct. A 2-mm probe 16B will then be used, followed by a 4-mm probe 16C to extend the full length of the meibomian gland. After initial MGP, the cannula will be inserted into each gland in the lid being treated to deliver 50% AS. Alternately, fewer preliminary probing steps could be employed. Preferably, information on the meibomian glands are collected and logged during the probing.

It is possible that MGP alone may not address a raw ductal epithelial defect. Healing of this defect may lead to subsequent minor narrowing of the duct diameter within months or years, with eventual redevelopment of pop/gritty sound with resistance upon re-probing. Hence, post-MGP use of intraductal AS is believed to promote rapid ductal re-epithelialization with restoration of ductal integrity, manifested not only by continued relief of symptoms, but also suppression or inhibition of pop/gritty sound resistance, which may promote or allow MG growth.

Other biological substance, in addition to, or in place of, AS, might possibly be introduced with similar beneficial effects. For instance, blood-derived allogeneic, umbilical cord and recombinant sera could be used. Similarly, platelet preparations, such as platelet rich plasma, platelet lysate/releasate and platelet concentrate could be used. Albumin, fresh frozen plasma and fibronectin are additional options. Stem cells, whether derived from blood or non-hematologic tissue might reasonably be expected to achieve a similar effect, as well as amniotic-derived fluid or cells.

The foregoing description of a preferred embodiment is provided for illustrative and exemplary purposes. The present invention is not necessarily limited thereto. Rather, those skilled in the art will appreciate that various modifications, as well as adaptations to particular circumstances, will fall within the scope of the invention as herein described and of the claims appended hereto.

What is claimed is:

1. A method of improving meibomian gland function in a patient, the method comprising:
   inserting a cannula into an interior of a meibomian gland of the patient through an orifice thereinto, the cannula including at least one opening in communication with the interior of the meibomian gland; and
   injecting a blood product into the interior of the meibomian gland through the inserted cannula via the at least one opening.

2. The method of claim 1, further comprising inserting at least one probe into the interior of the meibomian gland through the orifice prior to insertion of the cannula.

3. The method of claim 2, wherein inserting the at least one probe prior to insertion of the cannula includes inserting at least two probes of differing lengths prior to insertion of the cannula.

4. The method of claim 3, wherein inserting the at least two probes of differing lengths includes:
   first, inserting a 1-millimeter (mm) long probe;
   second, inserting a 2-mm long probe; and
   third, inserting a 4-mm long probe to a full length of the meibomian gland.

5. The method of claim 1, wherein injecting the blood product includes injecting autologous serum (AS).

6. The method of claim 5, wherein the AS is obtained using venipuncture.

7. The method of claim 5, wherein the AS is obtained using a finger prick.

8. The method of claim 5, wherein the AS is 50% AS.

9. The method of claim 1, wherein injecting the blood product includes injecting at least one of the following blood-derived sera:
   allogenic serum;
   umbilical cord serum; and
   recombinant serum.

10. The method of claim 1, wherein injecting the blood product includes injecting at least one of the following platelet preparations:
    platelet rich plasma;
    platelet lysate;
    platelet releasate; and
    platelet concentrate.

11. The method of claim 1, wherein injecting the blood product includes injecting fresh frozen plasma.

12. The method of claim 1, wherein injecting the blood product includes injecting at least one of albumin and fibronectin.

* * * * *